(12) United States Patent
Walton, III

(10) Patent No.: US 8,740,089 B2
(45) Date of Patent: *Jun. 3, 2014

(54) MEDICAL INFORMATION DEVICE AND SYSTEM AND METHOD OF USE

(71) Applicant: James F. Walton, III, Tallahassee, FL (US)

(72) Inventor: James F. Walton, III, Tallahassee, FL (US)

(*) Notice: Subject to any disclaimer, the term of this patent is extended or adjusted under 35 U.S.C. 154(b) by 0 days.

This patent is subject to a terminal disclaimer.

(21) Appl. No.: 14/048,645

(22) Filed: Oct. 8, 2013

(65) Prior Publication Data

US 2014/0039932 A1 Feb. 6, 2014

(51) Int. Cl.
*G06K 19/00* (2006.01)

(52) U.S. Cl.
USPC .......................................................... 235/487

(58) Field of Classification Search
USPC .......................................................... 235/487
See application file for complete search history.

(56) References Cited

U.S. PATENT DOCUMENTS

| | | | |
|---|---|---|---|
| 5,658,016 A | 8/1997 | Goeken | |
| D426,833 S | 6/2000 | Vanelli | |
| 6,513,720 B1 | 2/2003 | Armstrong | |
| 6,747,561 B1 | 6/2004 | Reeves | |
| 6,751,805 B1 | 6/2004 | Austion | |
| 6,845,063 B2 | 1/2005 | Mitchell | |
| 7,827,043 B2 | 11/2010 | Tahan | |
| 8,308,062 B1* | 11/2012 | Walton, III | 235/380 |
| 2002/0120470 A1 | 8/2002 | Trice, Sr. | |
| 2003/0058110 A1 | 3/2003 | Rich | |
| 2003/0101077 A1 | 5/2003 | Whol | |
| 2003/0150143 A1 | 8/2003 | Hazard | |
| 2005/0194270 A1 | 9/2005 | Gombar | |
| 2006/0010012 A1 | 1/2006 | Franzblau et al. | |
| 2006/0015368 A1 | 1/2006 | Hockey | |
| 2006/0085226 A1 | 4/2006 | Kamber | |
| 2006/0142057 A1 | 6/2006 | Schuler et al. | |
| 2007/0158411 A1 | 7/2007 | Krieg, Jr. | |
| 2007/0265884 A1 | 11/2007 | Lubell et al. | |
| 2008/0126729 A1 | 5/2008 | Cai et al. | |
| 2008/0319798 A1 | 12/2008 | Kelley | |
| 2009/0076849 A1 | 3/2009 | Diller | |
| 2009/0101721 A1 | 4/2009 | Hawthorne et al. | |
| 2009/0295569 A1 | 12/2009 | Corwin et al. | |
| 2010/0115609 A1 | 5/2010 | Spence | |

* cited by examiner

*Primary Examiner* — Christle I Marshall
(74) *Attorney, Agent, or Firm* — The Livingston Firm; Edwards M. Livingston, Esq.; Bryan L. Loeffler, Esq.

(57) ABSTRACT

A medical information device (1) and two dimensional bar code (2) for storing an individual's emergency medical information on and/or providing remote access to the medical information. The medical information device may be updated by an individual over the Internet by sending updated information to a central location that updates the information in a central database. The medical information device is capable of storing medical information directly therein and/or of providing remote access to medical information stored in a central database. This is accomplished by using a two-dimensional barcode 2, such as a Quick Response Code ("QR code") (3) or other matrix barcode, that is capable of storing text and/or URL information that may be opened by an electronic device or other imaging device, such as a smart phone.

16 Claims, 3 Drawing Sheets

MEDICAL INFORMATION DEVICE AND SYSTEM AND METHOD OF USE

CROSS-REFERENCE TO RELATED APPLICATIONS

This application is a continuation-in-part of application Ser. No. 13/658,102 filed on Oct. 23, 2012 which is currently pending and is a continuation-in-part of application Ser. No. 13/477,720 filed on Jun. 22, 2012 which is currently pending. The patent applications identified above are incorporated herein by reference in their entirety to provide continuity of disclosure.

FIELD OF THE INVENTION

This invention relates to providing personal medical information to first responders during an emergency and other medical personnel through the use of electronic devices and the internet.

BACKGROUND OF THE INVENTION

During a medical emergency, time is of the essence for a patient to receive the proper care from first responders. In such instances it is important that first responders are aware of a patient's medical history including allergies to drugs, current medications and medical conditions. It also becomes necessary to have the patient's emergency contact information and physician contact information. In many instances patients are unconscious and unable to provide any information to first responders. Conventional methods of providing such information include medical identification bracelets which may list an individual's allergies or medical conditions. However, only a limited amount of information can be included on such bracelets. There have also been attempts to store an individual's medical information on electronic storage devices such as flash drives or radio frequency identification cards ("RFID") in the past. However, many of these devices are complicated to use and to store information on. In addition, many of these devices are carried in wallets or on key chains and can easily be missed by a first responder. In addition, such devices may be damaged in certain situations, such as if the devices become wet during a medical emergency involving water or if the devices are near flames. A further problem with conventional devices occurs if an individual is injured in a foreign country, thereby rendering the electronic storage device useless because the information stored on the device is not written in the first responder's native language.

Therefore, the need exists for a personal medical information device and system and method of use that allows a first responder or other medical personnel to access an individual's medical information.

The relevant prior art includes the following references:

| Patent No. (U.S. Patent References) | Inventor | Issue/ Publication Date |
| --- | --- | --- |
| 7,827,043 | Tahan | Nov. 2, 2010 |
| 2010/0115609 | Spence | May 6, 2010 |
| 2009/0295569 | Corwin et al. | Dec. 3, 2009 |
| 2009/0101721 | Hawthorne et al. | Apr. 23, 2009 |
| 2009/0076849 | Diller | Mar. 19, 2009 |
| 2008/0126729 | Cai et al. | May 29, 2008 |
| 2008/0319798 | Kelley | Dec. 25, 2008 |
| 2007/0265884 | Lubell et al. | Nov. 15, 2007 |
| 2007/0158411 | Krieg, Jr. | Jul. 12, 2007 |
| 2006/0142057 | Schuler et al. | Jun. 29, 2006 |
| 2006/0085226 | Kamber | Apr. 20, 2006 |
| 2006/0015368 | Hockey | Jan. 19, 2006 |
| 2006/0010012 | Franzblau et al. | Jan. 12, 2006 |
| 2005/0194270 | Gombar | Sep. 8, 2005 |
| 6,845,063 | Mitchell | Jan. 18, 2005 |
| 6,751,805 | Austion | Jun. 22, 2004 |
| 6,747,561 | Reeves | Jun. 8, 2004 |
| 2003/0150143 | Hazard | Aug. 14, 2003 |
| 2003/0101077 | Whol | May 29, 2003 |
| 2003/0058110 | Rich | Mar. 27, 2003 |
| 6,513,720 | Armstrong | Feb. 4, 2003 |
| 2002/0120470 | Trice, Sr. | Aug. 29, 2002 |
| D426,833 | Vanelli | Jun. 20, 2000 |
| 5,658,016 | Goeken | Aug. 19, 1997 |
| 5,659,741 | Eberhardt | Aug. 19, 1997 |
| 5,337,290 | Ventimiglia et al. | Aug. 9, 1994 |
| 5,171,039 | Dusek | Dec. 15, 1992 |
| 4,575,127 | Michel | Mar. 11, 1986 |
| 4,491,725 | Pritchard | Jan. 1, 1985 |
| 4,318,554 | Anderson et al. | Mar. 9, 1982 |
| 3,792,542 | Cohan | Feb. 19, 1974 |

SUMMARY OF THE INVENTION

The primary object of the present invention is to provide an medical information device and system and method of use that allows a user to easily store personal and medical information in a central database.

Another object of the present invention is to provide an medical information device that is easily identifiable by a first responder as being a medical information device.

An additional object of the present invention is to provide an medical information device and system and method of use that provides a medical worker remote access to an individual's medical information.

The present invention fulfills the above and other objects by providing an medical information device for storing emergency medical information, such as blood type, allergies, medical conditions, present medications, age, doctor information and emergency contact information. The card is capable of storing medical information and/or access information so medical information may be accessed remotely. This is accomplished by using a two-dimensional barcode, such as a Quick Response Code ("QR code") or other matrix barcode, that is capable of storing text and/or URL information that may be opened by an electronic device or other imaging device, such as a smart phone. The two-dimensional barcode may be printed directly on a medical information device. Alternatively, the two-dimensional barcode may be printed on a bracelet, key chain and/or on an adhesive-backed material and then adhered to an existing card, such as a driver's license or other identification card, thereby making the existing card a medical information device.

The above and other objects, features and advantages of the present invention should become even more readily apparent to those skilled in the art upon a reading of the following detailed description in conjunction with the drawings wherein there is shown and described illustrative embodiments of the invention.

BRIEF DESCRIPTION OF THE DRAWINGS

In the following detailed description, reference will be made to the attached drawings in which.

DESCRIPTION OF THE PREFERRED EMBODIMENTS

Figure 1:
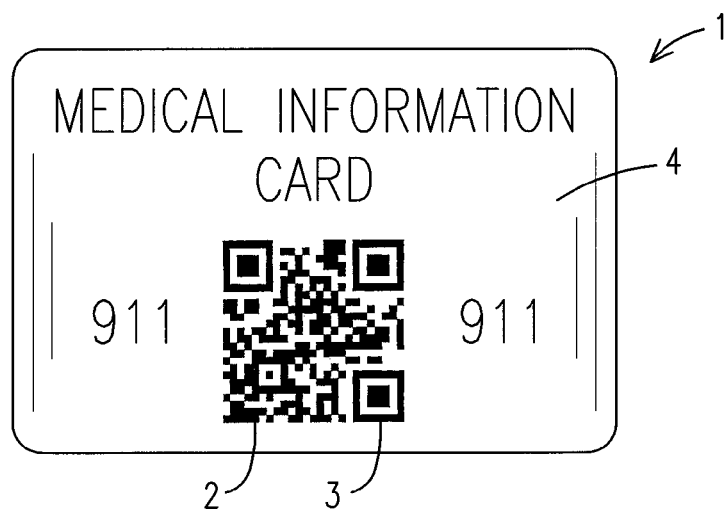
FIG. 1 is a front view of an identification card being used as a medical information device of the present invention.

With reference to FIG. 1, a front view of an identification card 4 being used as a medical information device 1 of the present invention is illustrated. The medical information device 1 allows an individual to store emergency medical information, such as blood type, allergies, medical conditions, present medications, age, doctor information and emergency contact information and to provide a means for retrieving that information to a first responder or other medical personnel. The medical information device 1 is capable of storing medical information directly therein and/or of providing remote access to medical information stored in a central database. This is accomplished by using a two-dimensional barcode 2, such as a Quick Response Code ("QR code") 3 or other matrix barcode, that is capable of storing text and/or URL information that may be opened by an electronic device or other imaging device, such as a smart phone. The two-dimensional barcode 2 may be printed directly on a medical information device 1, such as an identification card 4 (as illustrated here), a bracelet, a keychain and so forth.

Figure 2:
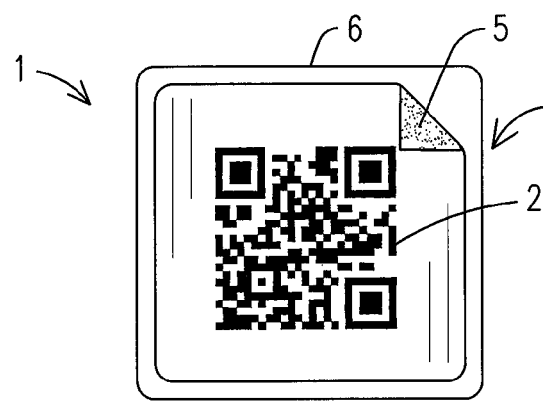
FIG. 2 is a front view of a two-dimensional barcode of the present invention printed on an adhesive-backed material.

With reference to FIG. 2, a front view of a two-dimensional barcode 2 of the present invention printed on an adhesive-backed material 5 is illustrated. The two-dimensional barcode 2 may have medical information directly stored therein and/or provide a URL for remote access of medical information stored in a central database. The two-dimensional barcode 2 illustrated here may be used by peeling off a backing 6 and adhering the adhesive backed material 5, such as paper, plastic, foil and so forth, to any object, such as an identification car, bracelet, keychain and so forth, thereby making the object a medical information device 1.

Figure 3:
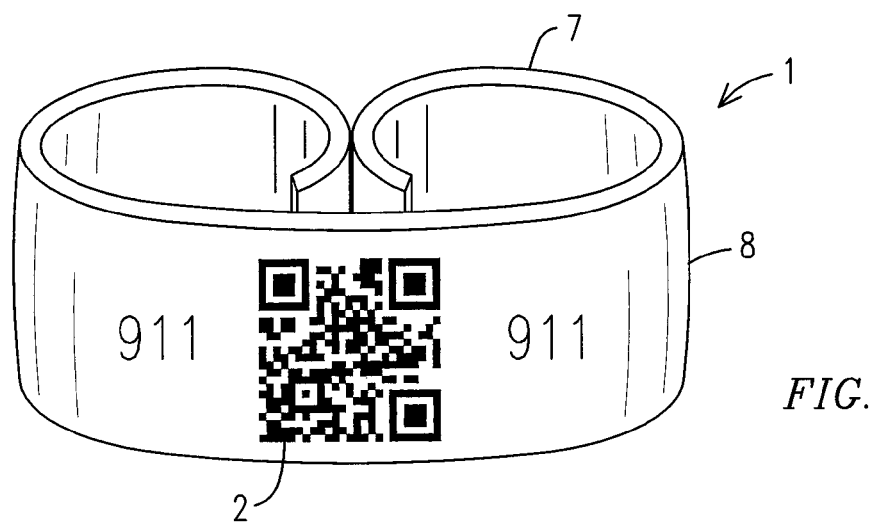
FIG. 3 is a front perspective view of a bracelet being used as a medical information device of the present invention.

With reference to FIG. 3, a front perspective view of a bracelet 7 being used as a medical information device 1 of the present invention is illustrated. The bracelet 7 may be a conventional bracelet 7 or a bracelet 7 that is a flexible bistable spring band 8 that may be sealed within a fabric or plastic cover. The bistable spring band 8 can be straightened out, making tension within the bistable spring band 8. The straightened bracelet 7 may then be pressed against the individual's forearm, causing the bistable spring band 8 to spring back into a curve that wraps around the wrist, securing the bracelet 7 to the wearer. A two-dimensional barcode 2 may be printed directly on the bracelet 7.

Figure 4:
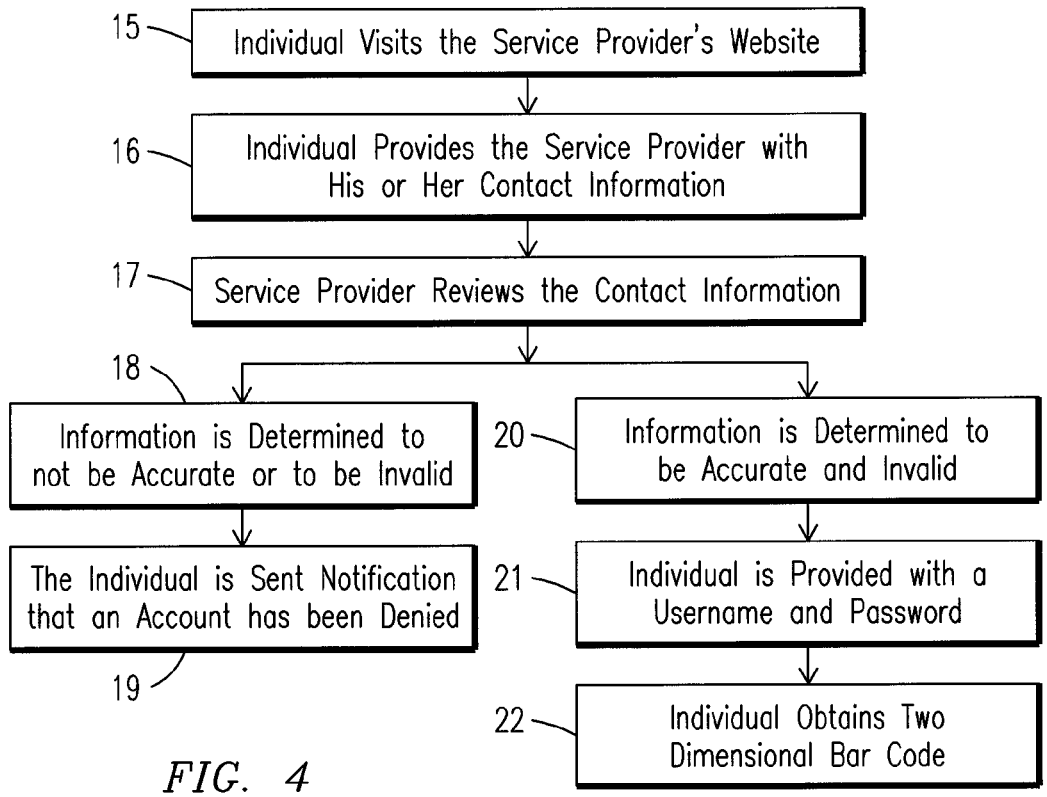
FIG. 4 is a flow chart showing an individual signing up for an account with a service provider that provides a medical information device to the individual.

With reference to FIG. 4, a flow chart showing an individual signing up for an account with a service provider that provides a medical information device to the individual is illustrated. First, the individual visits the service provider's website 15. Then, the individual provides the service provider with his or her contact information, which includes the individual's name, address, phone number, email address and so forth 16. The service provider then reviews the contact information to determine the accuracy of the information and the validity of the information 17. If the information is determined to not be accurate or to be invalid 18, then the individual is sent notification, preferably via email, that an account has been denied 19. If the information is determined to be accurate and valid 20, then the individual is sent an approval, preferably via email, that an account has been created and the individual is provided with a username and password 21. Next, the individual is provided with a medical information device having a two dimensional barcode printed thereon and/or with a adhesive backed two dimensional barcode 22.

Figure 5:
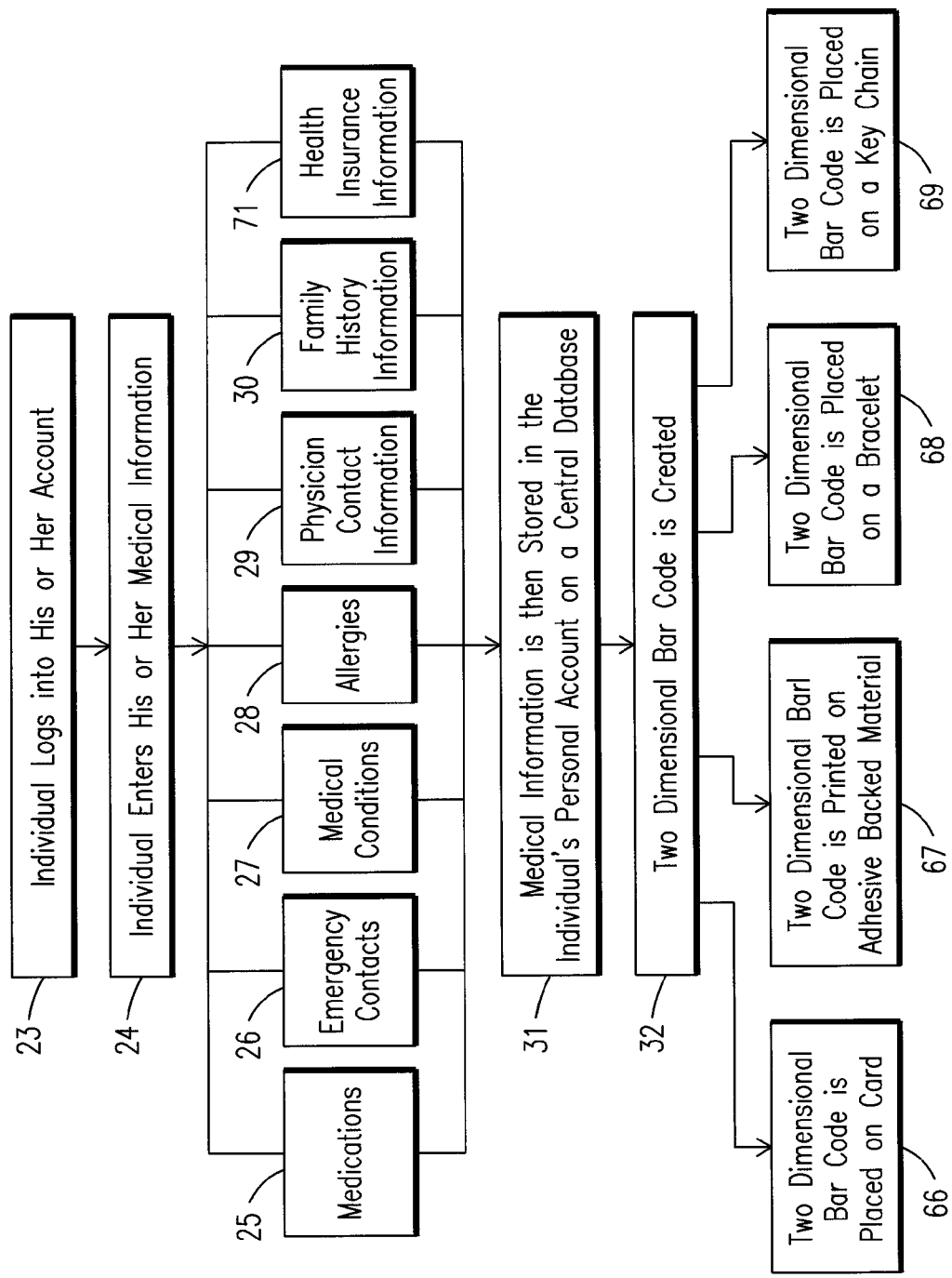
FIG. 5 is a flow chart showing the system and method of the present invention in which an individual enters medical information into an online account.

With reference to FIG. 5, a flow chart showing the system and method of the present invention in which an individual enters medical information into an online account is illustrated. First, the individual logs into his or her account using the username and password provided by the service provider 23. Then, the individual enters his or her medical information 24, which includes medications 25, emergency contacts 26, medical conditions 27, allergies 28, physician contact information 29, family history information 30, health insurance information 71 and so forth. The medical information is then stored in the individual's personal account on a central database 31. A two dimensional bar code is then created that is personalized to the individual's account and has text medical information and/or a URL that directs a user to the individual's medical information remotely after the two dimensional bar code is scanned 32. The two dimensional bar code may be printed on an identification card 66, an adhesive backed material 67, a bracelet 68 and/or a keychain 69.

Figure 6:
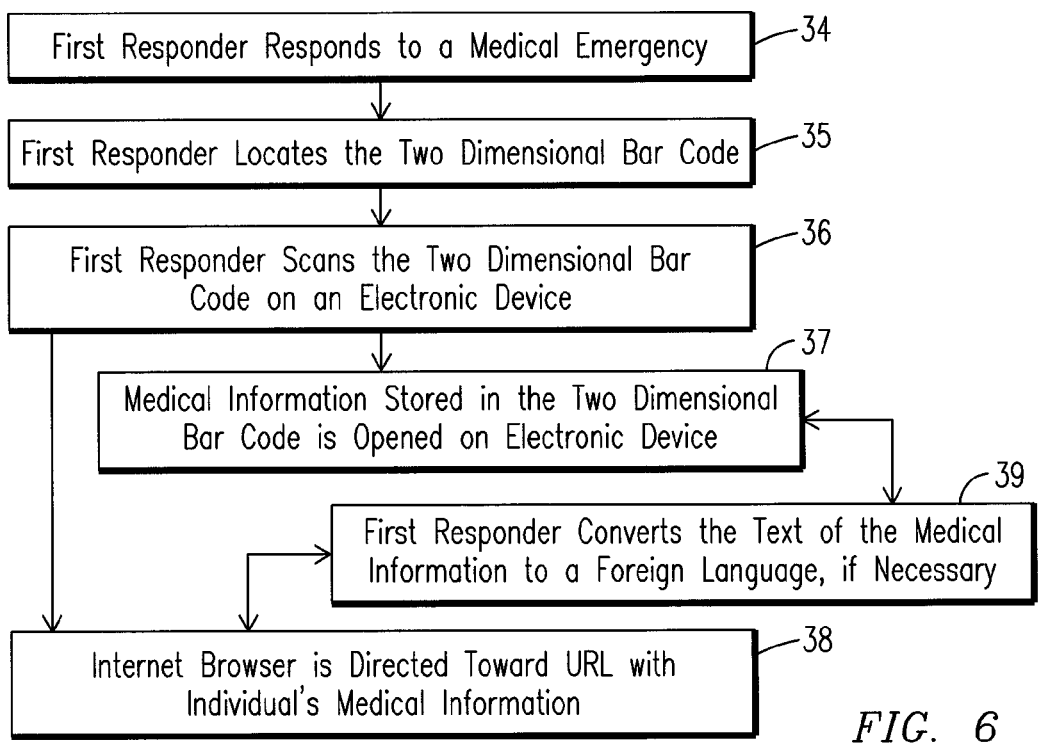
FIG. 6 is a flowchart showing the system and method of the present invention in which a first responder retrieves medical information from a patient's medical information device.

With reference to FIG. 6, a flowchart showing the system and method of the present invention in which a first responder retrieves medical information from a patient's medical information device is illustrated. First, a first responder responds to a medical emergency 34. Then, the first responder locates the two dimensional bar code 35. Next, the first responder scans the two dimensional bar code using an electronic device 36. Then, the medical information stored in the two dimensional bar code as text is opened on the electronic device 37 and/or the an Internet browser on the electronic device is directed to a URL where the individual's medical information stored in the central database is accessible 38. The first responder may also convert the medical information to a foreign language if the patient has been injured or is receiving medical care in a foreign country 39.

It is to be understood that while a preferred embodiment of the invention is illustrated, it is not to be limited to the specific form or arrangement of parts herein described and shown. It will be apparent to those skilled in the art that various changes may be made without departing from the scope of the invention and the invention is not to be considered limited to what is shown and described in the specification and drawings.

Having thus described my invention, I claim:

1. A method for using a medical information device for storing medical information and providing medical information to first responders and medical personnel comprising the steps of:
   a. the individual providing a service provider with his or her contact information;
   b. the service provider reviewing the contact information and rendering a decision on whether to allow the individual to have an account;
   c. an individual creating an account with a service provider over the internet;

d. the individual's medical information being provided to the service provider to be saved in a central database; the individual obtaining a two dimensional bar code; and
e. the individual obtaining a two dimensional bar code that is personalized to the individual's account.

2. The method of claim 1 further comprising steps of:
the service provider deciding to allow the individual to have an account; and
the service provider creating an account and providing the individual with a username and password.

3. The method of claim 1 further comprising steps of:
a first responder scanning the two dimensional bar code using an electronic device and obtaining the individual's medical information.

4. The method of claim 3 further comprising a step of:
the first responder translating the medical information to a foreign language using the electronic device.

5. The method of claim 1 wherein:
said two dimensional bar code is located on an identification card.

6. The method of claim 1 wherein:
said two dimensional bar code is located on an adhesive backed material.

7. The method of claim 1 wherein:
said two dimensional bar code is located on a bracelet.

8. The method of claim 1 wherein:
said two dimensional bar code is located on a key chain.

9. A system for using a medical information device for storing medical information and providing medical information to first responders and medical personnel comprising:
the individual providing a service provider with his or her contact information;
the service provider reviewing the contact information and rendering a decision on whether to allow the individual to have an account;
an individual creating an account with a service provider over the internet;
the individual obtaining a medical information device;
the individual's medical information being provided to the service provider to be saved in a central database; the individual obtaining a two dimensional bar code; and
the individual obtaining a two dimensional bar code that is personalized to the individual's account.

10. The system of claim 9 further comprising:
the service provider deciding to allow the individual to have an account; and
the service provider creating an account and providing the individual with a username and password.

11. The system of claim 9 further comprising:
a first responder scanning the two dimensional bar code using an electronic device and obtaining the individual's medical information.

12. The system of claim 11 further comprising:
the first responder translating the medical information to a foreign language using the electronic device.

13. The system of claim 9 wherein:
said two dimensional bar code is located on an identification card.

14. The system of claim 9 wherein:
said two dimensional bar code is located on an adhesive backed material.

15. The system of claim 9 wherein:
said two dimensional bar code is located on a bracelet.

16. The system of claim 9 wherein:
said two dimensional bar code is located on a key chain.

* * * * *